(12) United States Patent
Qadeer

(10) Patent No.: US 11,911,005 B2
(45) Date of Patent: Feb. 27, 2024

(54) ENDOSCOPIC RETRACTION ASSIST DEVICES AND RELATED SYSTEMS AND METHODS

(71) Applicant: Applied EndoSolutions, LLC, Northfield, IL (US)

(72) Inventor: Mohammed A. Qadeer, Northfield, IL (US)

(73) Assignee: Applied EndoSolutions, LLC, Northfield, IL (US)

( * ) Notice: Subject to any disclaimer, the term of this patent is extended or adjusted under 35 U.S.C. 154(b) by 72 days.

(21) Appl. No.: 17/514,319

(22) Filed: Oct. 29, 2021

(65) Prior Publication Data
US 2023/0137851 A1    May 4, 2023

(51) Int. Cl.
*A61B 1/00*    (2006.01)
*A61B 1/018*    (2006.01)

(52) U.S. Cl.
CPC ............ *A61B 1/018* (2013.01); *A61B 1/0014* (2013.01); *A61B 1/00147* (2013.01)

(58) Field of Classification Search
CPC ... A61B 1/018; A61B 1/0014; A61B 1/00147; A61B 2017/00473; A61B 1/00101; A61B 1/0008; A61M 25/0067; A61M 25/0082
USPC .......................... 600/102, 104, 153, 129, 114
See application file for complete search history.

(56) References Cited

U.S. PATENT DOCUMENTS

| | | | |
|---|---|---|---|
| 3,915,157 A | 10/1975 | Mitsui | |
| 4,636,346 A | 1/1987 | Gold et al. | |
| 5,667,480 A * | 9/1997 | Knight | A61B 17/00234 606/190 |
| 5,865,726 A * | 2/1999 | Katsurada | A61B 1/12 600/129 |
| 6,352,503 B1 | 3/2002 | Matsui et al. | |
| 6,527,753 B2 | 3/2003 | Sekine et al. | |
| 7,169,115 B2 | 1/2007 | Nobis et al. | |
| 7,575,548 B2 * | 8/2009 | Takemoto | A61B 1/018 600/122 |
| 8,187,170 B2 | 5/2012 | Naito | |
| 8,562,512 B2 * | 10/2013 | Menn | A61B 1/0014 600/102 |
| 9,565,998 B2 | 2/2017 | Piskun et al. | |
| 10,779,708 B2 | 9/2020 | Qadeer | |
| 2007/0173687 A1 | 7/2007 | Shima et al. | |
| 2007/0270643 A1 | 11/2007 | Nobis et al. | |

(Continued)

FOREIGN PATENT DOCUMENTS

CN    110974355 B    2/2021

OTHER PUBLICATIONS

"A Novel Flexible Over-tube for Advanced Endoscopic Intervention Under Stabilized Visualization With Adjustable Tissue Traction", https://www.sages.org/meetings/annual-meeting/abstracts-archive/a-novel-flexible-over-tube-for-advanced-endoscopic-intervention-under-stabilized-visualization-with-adjustable-tissue-traction/, 2012, 2 pages.

*Primary Examiner* — Timothy J Neal
*Assistant Examiner* — James Edward Boice
(74) *Attorney, Agent, or Firm* — Myers Bigel, P.A.

(57) ABSTRACT

An endoscopic retraction assist device includes a body comprising opposite proximal and distal end portions and a central portion between the proximal and distal end portions, and a device channel defined in the body. At the central portion of the body, the device channel transitions from a circular portion having a circular cross section or perimeter to an arcuate portion having an elongated arcuate cross section or perimeter.

18 Claims, 6 Drawing Sheets

(56) References Cited

U.S. PATENT DOCUMENTS

| | | |
|---|---|---|
| 2008/0262301 A1 | 10/2008 | Gibbons et al. |
| 2009/0048486 A1 | 2/2009 | Surti |
| 2009/0227843 A1 | 9/2009 | Smith et al. |
| 2010/0113878 A1 | 5/2010 | Kawano |
| 2011/0092766 A1 | 4/2011 | Bapaye et al. |
| 2012/0095291 A1 | 4/2012 | Nakajima |
| 2016/0120395 A1 | 5/2016 | Qi |
| 2016/0166343 A1 | 6/2016 | Poon et al. |
| 2016/0338681 A1 | 11/2016 | Smith et al. |
| 2017/0105797 A1 | 4/2017 | Mikkaichi |
| 2017/0360281 A1 | 12/2017 | Ponsky |

\* cited by examiner

ENDOSCOPIC RETRACTION ASSIST DEVICES AND RELATED SYSTEMS AND METHODS

BACKGROUND

Endoscopic submucosal dissection (ESD) is an evolving technique in the field of advanced endoscopy. Endoscopic Intramural Surgery (EIS) is one of the newest branches of gastrointestinal endoscopy and has a bright future. In this technique, a small opening is made in the inner layer of the gastrointestinal wall followed by the passage of the endoscope through that small opening either into the wall or sometimes outside the wall to preform dissections/removal of tissue. Upon completion of the procedure, the small opening is closed completely. Thus, it is a true minimally invasive surgery. Different procedures that fall under the category of EIS are endoscopic submucosal dissection (ESD), per oral endoscopic myotomy (POEM), and others.

EIS has been gradually growing in popularity all over the world due to its many advantages including lower risk of complications, decreased costs, faster recovery, and at the same time providing equivalent efficacy compared with open surgery or laparoscopic/robotic surgery. Despite its many advantages, the acceptance of EIS amongst gastrointestinal endoscopists is slow due to lack of proper devices to facilitate the process.

SUMMARY

Some embodiments of the present invention are directed to an endoscopic retraction assist device including: a body including opposite proximal and distal end portions and a central portion between the proximal and distal end portions; and a device channel defined in the body. At the central portion of the body, the device channel may transition from a circular portion having a circular cross section or perimeter to an arcuate portion having an elongated arcuate cross section or perimeter.

In some embodiments, the arcuate portion of the device channel is closer to the distal end portion of the body than is the circular portion of the device channel. The distal end portion of the body may include a ledge extending between the arcuate portion of the device channel and a distal end of the body. The ledge may be arcuate and may optionally widen from the arcuate portion of the device channel to the distal end of the body.

In some embodiments, the device channel defines a longitudinal axis, the body includes a top wall, a bottom wall, and first and second opposite side walls, and the bottom wall extends further in a first direction along or parallel to the longitudinal axis from the central portion toward a distal end of the body than do the top wall and the first and second side walls. The distal end portion of the body may widen from the central portion of the body toward the distal end of the body.

In some embodiments, the arcuate portion of the device channel has a maximum width that is 2-5 times a width or diameter of the circular portion of the device channel.

In some embodiments, the body is formed of a flexible and resilient material.

In some embodiments, the device and/or the body include a clip including first and second spaced apart arms extending downwardly from the proximal end portion of the body. The clip may be configured to releasably and slidably hold an endoscope therein.

In some embodiments, the proximal end portion of the body is configured to receive a tube through which a retraction device can be received.

In some embodiments, the body is monolithic.

Some other embodiments of the present invention are directed to an endoscope system including a tip. The tip includes: a body including opposite proximal and distal end portions and a central portion between the proximal and distal end portions; a clip including first and second spaced apart arms extending downwardly from the proximal end portion of the body; and a device channel defined in the body. The system includes an endoscope received in the clip and a retraction device received in the device channel. At the central portion of the body, the device channel may transition from a circular portion having a circular cross section or perimeter to an arcuate portion having an elongated arcuate cross section or perimeter.

In some embodiments, the endoscope has a lengthwise instrument channel defined therein, and the system may further include a dissection device received in the instrument channel.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION

Figure 1:
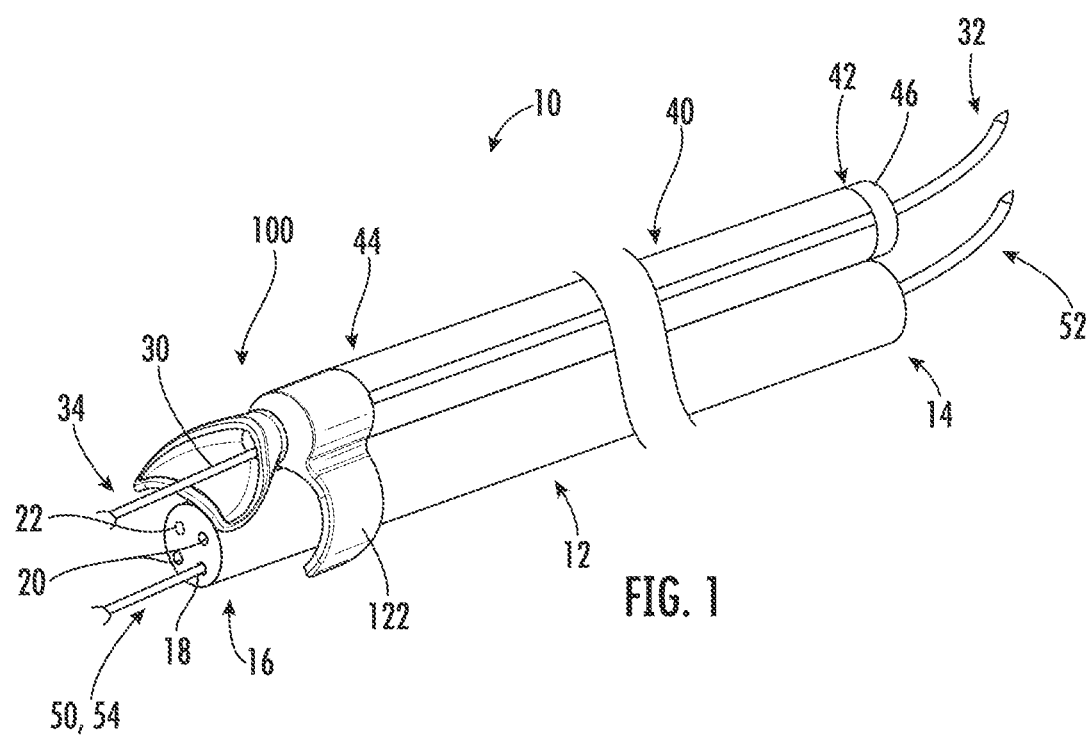
FIG. 1 is a perspective view of an endoscope system according to some embodiments of the present invention.
Figure 2:
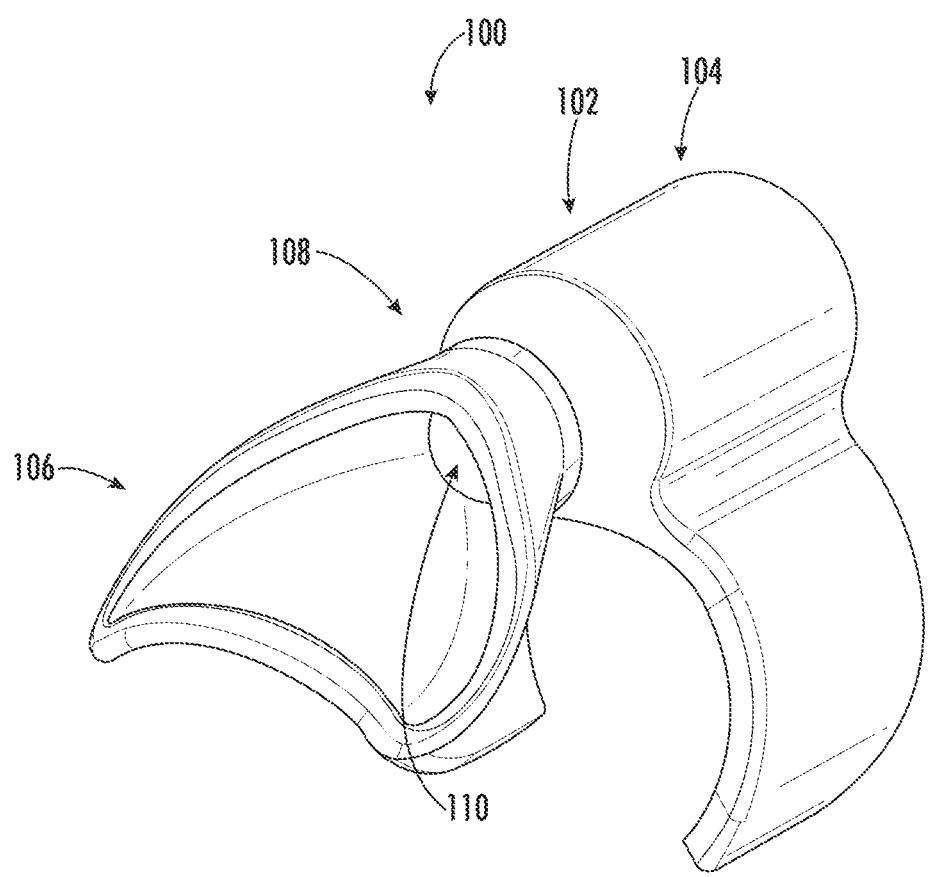
FIG. 2 is a perspective view of a tip of the system of FIG. 1.
Figure 3:
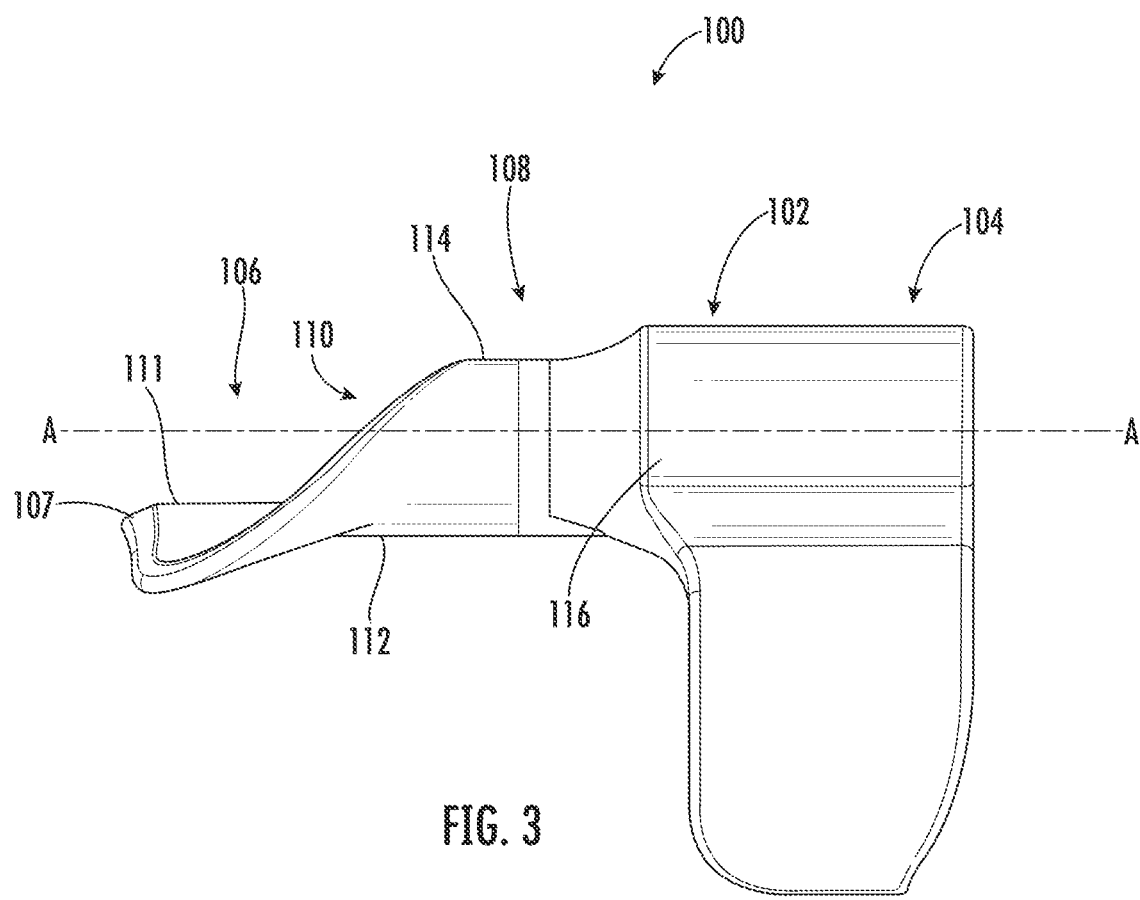
FIG. 3 is a side view of the tip of FIG. 2.
Figure 4:
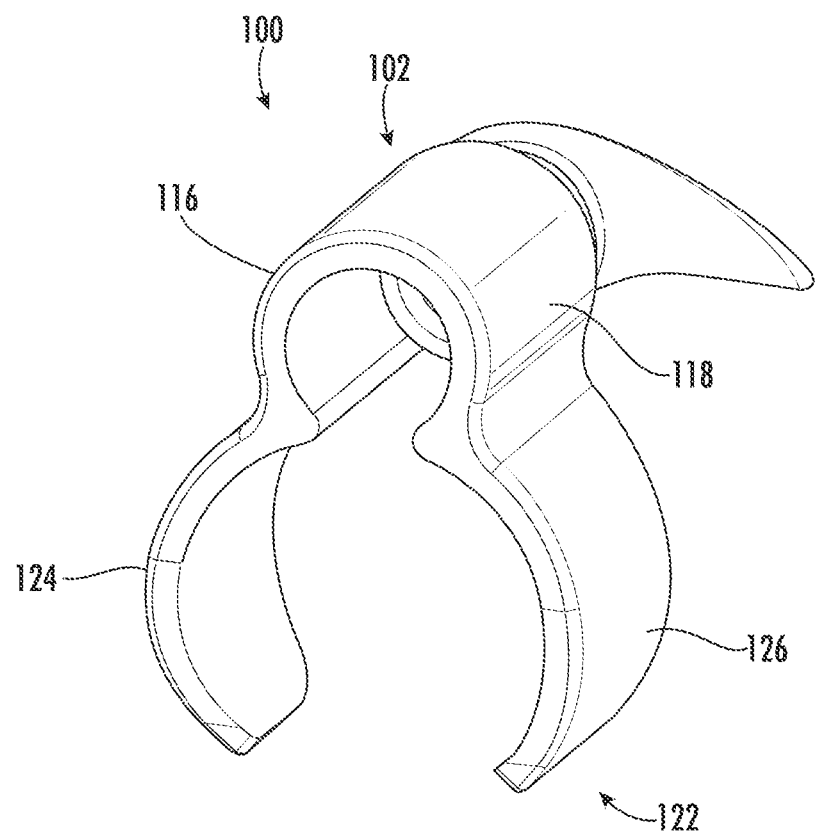
FIG. 4 is another perspective view of the tip of FIG. 2.
Figure 5:
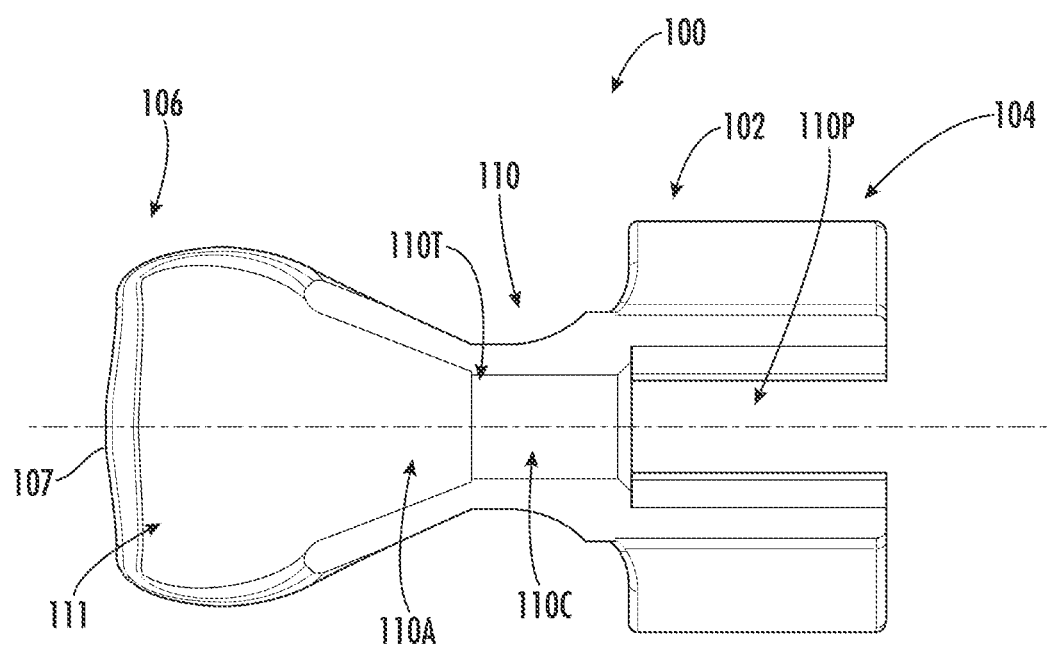
FIG. 5 is a top sectional view of the tip of FIG. 2.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

An endoscope system 10 according to some embodiments is illustrated in FIG. 1. The system 10 includes a tip 100 (which may also be referred to herein as an "Endoscopic Retraction Assist Device" or "ERAD").

As described in more detail below, an endoscope 12 may be held by the tip 100. The endoscope 12 includes opposite proximal and distal end portions 14, 16. An instrument channel 18 (e.g., working channel) may extend lengthwise through the endoscope 12 between the proximal and distal end portions 14, 16. The endoscope 12 may include one or more illumination windows 20 and an observation window 22 at the distal end portion 16 thereof.

A device or instrument 30 such as a retraction device may be received in a channel of the tip 100. The retraction device 30 includes opposite proximal and distal end portions 32, 34. An operator may control or manipulate the first retraction device 30 at the proximal end portion 32 as understood by those skilled in the art.

The device 30 may be received in and extend through an elongated tube 40. The tube 40 includes opposite proximal and distal end portions 42, 44. The distal end portion 44 of the tube 40 may connect to the tip 100 and the proximal end portion 32 of the device 30 may extend from the proximal end portion 42 of the tube 40. A stopper 46 may be at the proximal end portion 42 of the tube 40 and the device 30 may extend through the stopper 46. The stopper 46 is an air leak prevention device that allows the passage of instruments used for retraction.

A device or instrument 50 such as a dissection device may be received in the instrument channel 18 of the endoscope 12. The dissection device 50 includes opposite proximal and distal end portions 52, 54. An operator may control or manipulate the dissection device 50 at the proximal end portion 52 as understood by those skilled in the art.

Referring now to FIGS. 2-6, the tip 100 has a body 102. The body 102 includes opposite proximal and distal end portions 104, 106. The body 102 includes a central portion 108 between the proximal and distal end portions 104, 106.

A device or instrument channel or passageway 110 is defined in the body 102. The channel 110 defines a longitudinal axis A of the tip 100.

The channel 110 may be considered to have several portions or sections. A proximal portion 110P of the channel 110 at the proximal end portion 104 of the body 102 may have a circular cross section or perimeter and may have a constant diameter. A transitional portion 110T of the channel 110 at the central portion 108 of the body 102 may transition from a circular portion 110C having a circular cross section or perimeter to an arcuate portion 110A having an arcuate cross section or perimeter.

Figure 6:
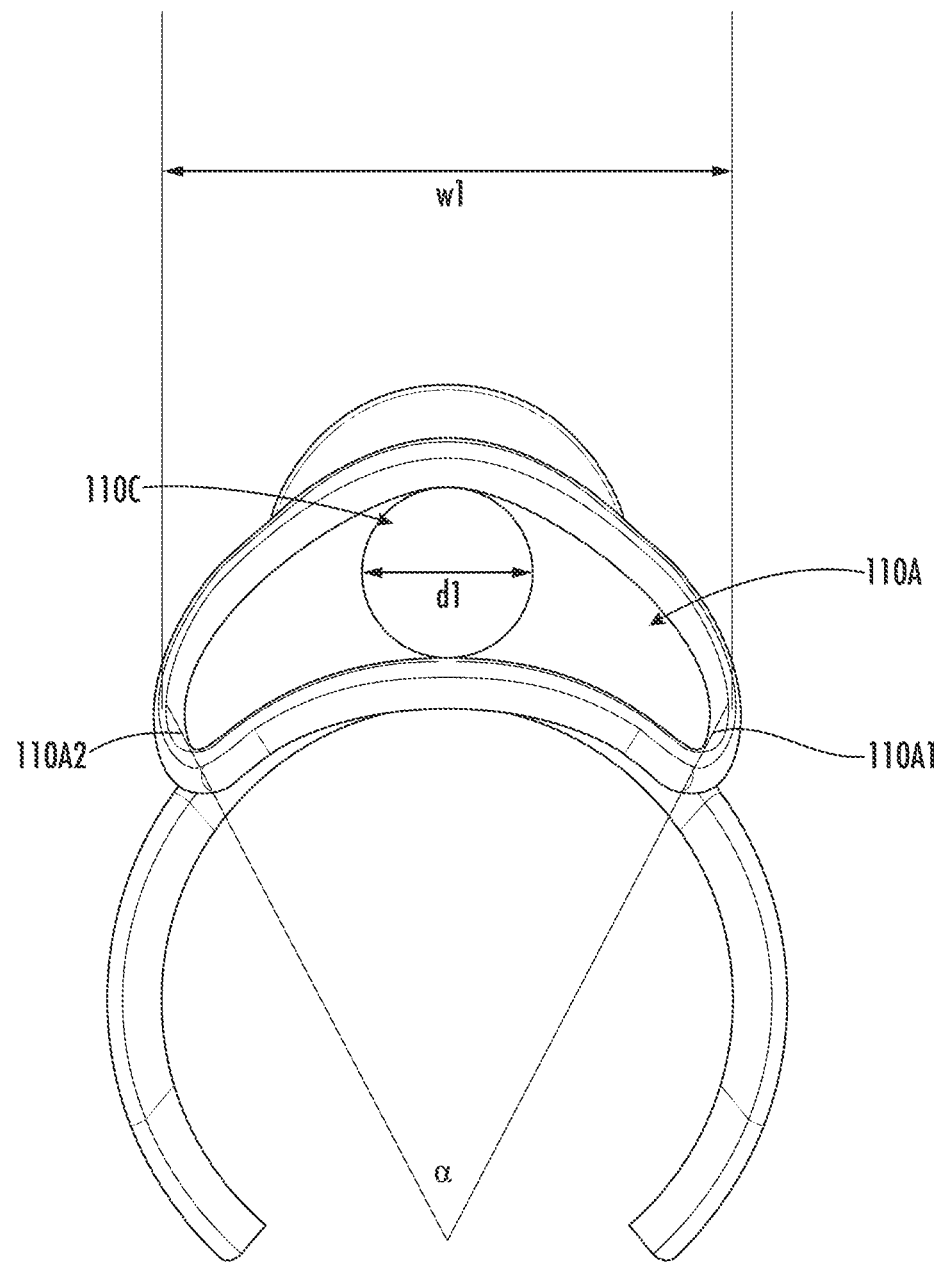
FIG. 6 is a front end view of the tip of FIG. 2.

The arcuate portion 110A of the channel 110 may increase in width in a longitudinal direction extending from the circular portion 110C of the channel 110 to a distal end 107 of the body 102. Referring to FIG. 6, the arcuate portion 110A of the channel 110 may have a maximum width w1 that is 2-5 times a diameter or width d1 of the circular portion 110C of the channel 110.

In some embodiments, the distal end portion 106 of the body 102 includes a ledge 111 extending between the arcuate portion 110A of the channel 110 and the distal end 107 of the body 102. The ledge 111 may be arcuate (e.g., inverse U-shape) and may widen from the arcuate portion 110A of the channel 110 to the distal end 107 of the body 102.

The body 102 may include, and the channel 110 may be at least partially defined by, a bottom or lower surface or wall 112, a top or upper surface or wall 114 that is opposite the bottom wall 112, a first side surface or wall 116, and/or a second side surface or wall 118 that is opposite the first side wall 116.

The bottom wall 112 may extend further longitudinally from the central portion 108 of the body 102 toward the distal end portion 106 of the body 102 than does the top wall 114 and the side walls 116, 118. In some embodiments, the distal end portion 106 of the body including the distal end 107 thereof only includes the bottom wall 112 (e.g., the ledge 111) and does not include the top wall 114 and the side walls 116, 118.

A clip 122 may be at the proximal end portion 104 of the body 102. The clip 122 may include a first arm 124 extending downwardly from the first side wall 116 of the body 102 and a second arm 126 extending downwardly from the second side wall 118 of the body 102. The clip 122 may be configured to releasably and/or slidably hold an endoscope (e.g., the endoscope 12 in FIG. 1).

The proximal end portion 104 of the body 102 is configured to receive an elongated member such as the tube 40 shown in FIG. 1. For example, the tube may be received and held in the proximal end portion 110P of the channel 110. A device such as the retraction device 30 shown in FIG. 1 may be received in the tube 40.

The tip 100 may be moveable or slidable relative to the endoscope 12 ex vivo but the tip 100 and the endoscope 12 may move as a single unit in vivo.

The tip body 102 may be formed of a flexible material such as a polymeric, plastic, and/or silastic material. The tip body 102 may be resilient. The tip body 102 may be transparent or translucent.

Referring to FIG. 6, the arcuate portion 110A of the channel 110 has an arcuate cross section or perimeter (e.g., in a plane perpendicular to the longitudinal axis A). The arcuate portion 110A of the channel 110 is elongated and includes opposite first and second end surfaces 110A1, 110A2. Referring to FIG. 6, an angle α may be defined between the first and second end surfaces 110A1, 110A2. The angle α may be at the center of curvature of the channel 110 and may be between 40 degrees and 80 degrees and, in some embodiments, is about 60 degrees. The configuration with the elongated arcuate channel allows the retraction device received in the channel to translate along the elongated arcuate profile of the channel between the first and second end surfaces thereof.

Referring to FIG. 1, in use, the tip 100 is attached to the endoscope 12 by receiving the endoscope 12 in the clip 122. The endoscope 12 with the attached tip 100 is then passed inside a gastrointestinal lumen. The tip 100 is made of a flexible material that bends in narrow areas, but is resilient and springs back to its original shape when the pressure of the narrow space is reduced. Thus, passage of the tip 100 through the narrow lumen is non-traumatic, and the presence of memory shape will keep its functionality intact.

The tip 100 acts as an external channel for passing the tissue retractor device 30 and thus the tip 100 acts as a tissue retractor assist device. Due to the presence of arcuate and longitudinal channel features, both horizontal and vertical movements of the retractor device 30 are possible, thus moving the retracted tissue in multiple directions to assist in dissection. This provides dynamic tissue retraction thus facilitating the dissection and increasing the speed of dissection.

The fact that the different ends or surfaces (lower, upper, sides) end or terminate at different distances from the proximal end of the tip gives the device 30 that extends out of the channel 110 the flexibility and maneuverability during tissue retraction.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

The invention claimed is:

1. An endoscopic retraction assist device comprising:
a body comprising opposite proximal and distal end portions and a central portion between the proximal and distal end portions; and
a device channel defined in the body,
wherein, at the central portion of the body, the device channel transitions from a circular portion having a circular cross section or perimeter to an arcuate portion having an elongated arcuate cross section or perimeter,
wherein the distal end portion of the body comprises a ledge extending between the arcuate portion of the device channel and a distalmost end of the body, and
wherein the ledge is arcuate and widens from the arcuate portion of the device channel to the distalmost end of the body.

2. The device of claim 1 wherein the arcuate portion of the device channel is closer to the distal end portion of the body than is the circular portion of the device channel.

3. The device of claim 1 wherein the device channel defines a longitudinal axis, the body comprises a top wall, a bottom wall, and first and second opposite side walls, and wherein the bottom wall extends further in a first direction along or parallel to the longitudinal axis from the central portion toward a distal end of the body than do the top wall and the first and second side walls.

4. The device of claim 3 wherein the distal end portion of the body widens from the central portion of the body toward the distal end of the body.

5. The device of claim 1 wherein the arcuate portion of the device channel has a maximum width that is 2-5 times a width or diameter of the circular portion of the device channel.

6. The device of claim 1 wherein the body is formed of a flexible and resilient material.

7. The device of claim 1 further comprising a clip including first and second spaced apart arms extending downwardly from the proximal end portion of the body.

8. The device of claim 7 wherein the clip is configured to releasably and slidably hold an endoscope therein.

9. The device of claim 7 wherein the body comprises the clip.

10. The device of claim 7 wherein the ledge is upwardly convex in a direction opposite a direction in which the first and second spaced apart arms extend downwardly from the proximal end portion of the body.

11. The device of claim 1 wherein the proximal end portion of the body is configured to receive a tube through which a retraction device can be received.

12. The device of claim 1 wherein the body is monolithic.

13. The device of claim 1 wherein the body comprises, and the device channel is defined by, a top wall, a bottom wall, and first and second opposite side walls.

14. The device of claim 1 wherein the device channel defines a longitudinal axis, and the body is symmetrical about the longitudinal axis.

15. The device of claim 1 wherein the device channel defines a longitudinal axis, and a middle longitudinally extending portion of the ledge extends closer to the longitudinal axis than do opposite longitudinally extending lateral edge portions of the ledge.

16. The device of claim 1 wherein the ledge continuously widens from the arcuate portion of the device channel to the distalmost end of the body.

17. An endoscope system comprising:
a tip comprising:
a body comprising opposite proximal and distal end portions and a central portion between the proximal and distal end portions;
a clip including first and second spaced apart arms extending downwardly from the proximal end portion of the body; and
a device channel defined in the body,
an endoscope received in the clip; and
a retraction device received in the device channel, wherein, at the central portion of the body, the device channel transitions from a circular portion having a circular cross section or perimeter to an arcuate portion having an elongated arcuate cross section or perimeter, wherein the distal end portion of the body comprises a ledge extending between the arcuate portion of the device channel and a distalmost end of the body, and wherein the ledge is arcuate and widens from the arcuate portion of the device channel to the distalmost end of the body.

18. The system of claim 17, wherein the endoscope has a lengthwise instrument channel defined therein, the system further comprising a dissection device received in the instrument channel.

\* \* \* \* \*